US005509805A

United States Patent [19]
Jagmin

[11] Patent Number: 5,509,805
[45] Date of Patent: Apr. 23, 1996

[54] RADIOGRAPHICALLY READABLE INFORMATION CARRIER AND METHOD OF USING THE SAME

[76] Inventor: Gary E. Jagmin, 875 St. Andrews Way, Frankfort, Ill. 60423

[21] Appl. No.: 153,318

[22] Filed: Nov. 16, 1993

[51] Int. Cl.⁶ .................................................. A61C 3/00
[52] U.S. Cl. ........................................ 433/215; 433/229
[58] Field of Search ..................................... 433/215, 229; 40/300, 301, 302, 303, 304

[56] References Cited

U.S. PATENT DOCUMENTS

| | | | |
|---|---|---|---|
| 4,027,391 | 6/1977 | Samis | 433/229 |
| 4,208,795 | 6/1980 | Muhlemann et al. | 433/229 X |
| 4,512,744 | 4/1985 | Michnick et al. | 433/229 |
| 4,557,693 | 12/1985 | Elggren | 433/229 |
| 4,797,101 | 1/1989 | Morris | 433/215 X |
| 4,913,654 | 4/1990 | Morgan et al. | 433/8 |
| 5,044,955 | 9/1991 | Jagmin | 433/229 |

FOREIGN PATENT DOCUMENTS

| | | | |
|---|---|---|---|
| 8600213 | 1/1986 | WIPO | 433/229 |
| 8904642 | 6/1989 | WIPO | 433/229 |

Primary Examiner—Nicholas D. Lucchesi
Attorney, Agent, or Firm—Potthast & Ring

[57] ABSTRACT

An identification apparatus (10) having a personal information carrier (12) having information carried by a radiopaque configuration (12) which is radiographically discernable with the personal information carrier (10) secured to an external and noninvasive portion of a tooth (14) and to provide a method for radiographically marking a person with individual information, having the steps of providing a personal information carrier (10) having information carried by a radiopaque configuration (12) which is radiographically readable by conventional dental X-ray techniques and securing the personal information carrier (12) to an external and noninvasive portion of a tooth (14).

55 Claims, 2 Drawing Sheets

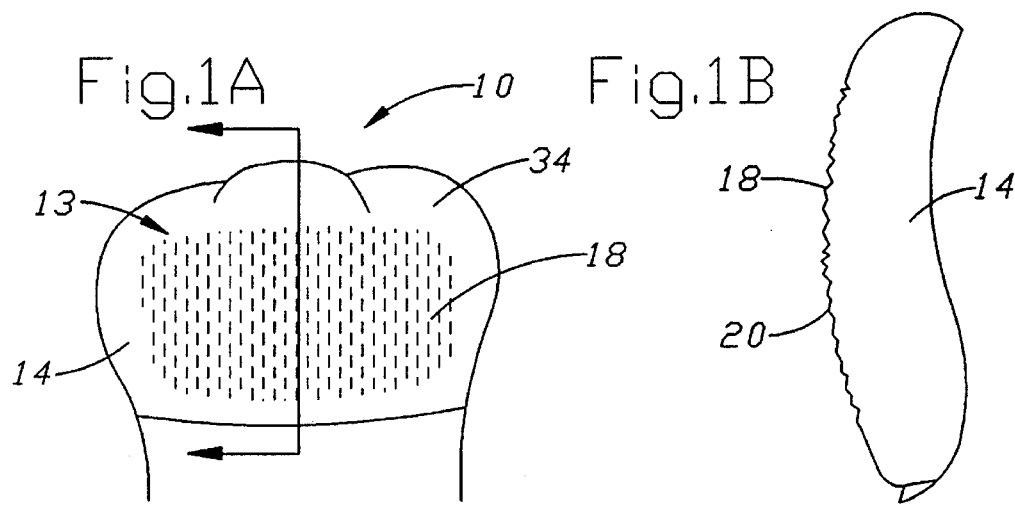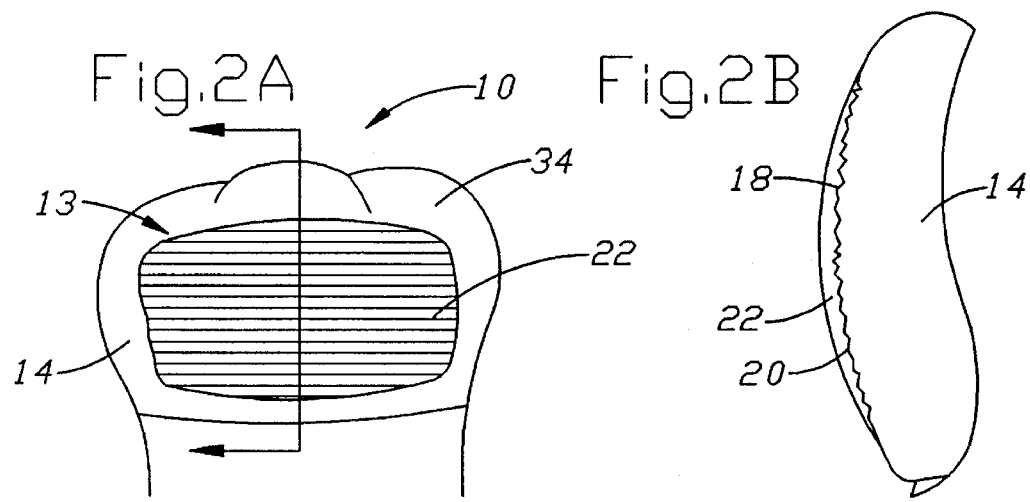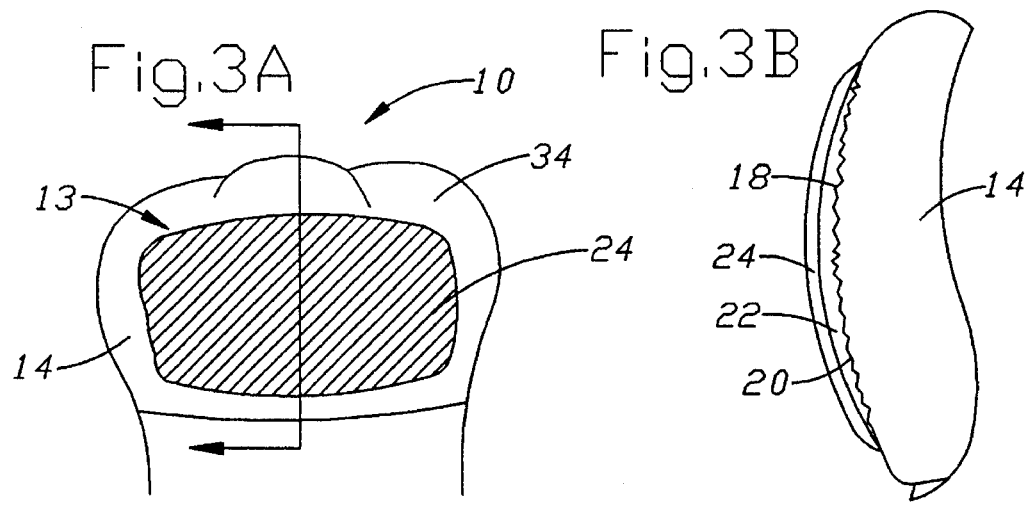

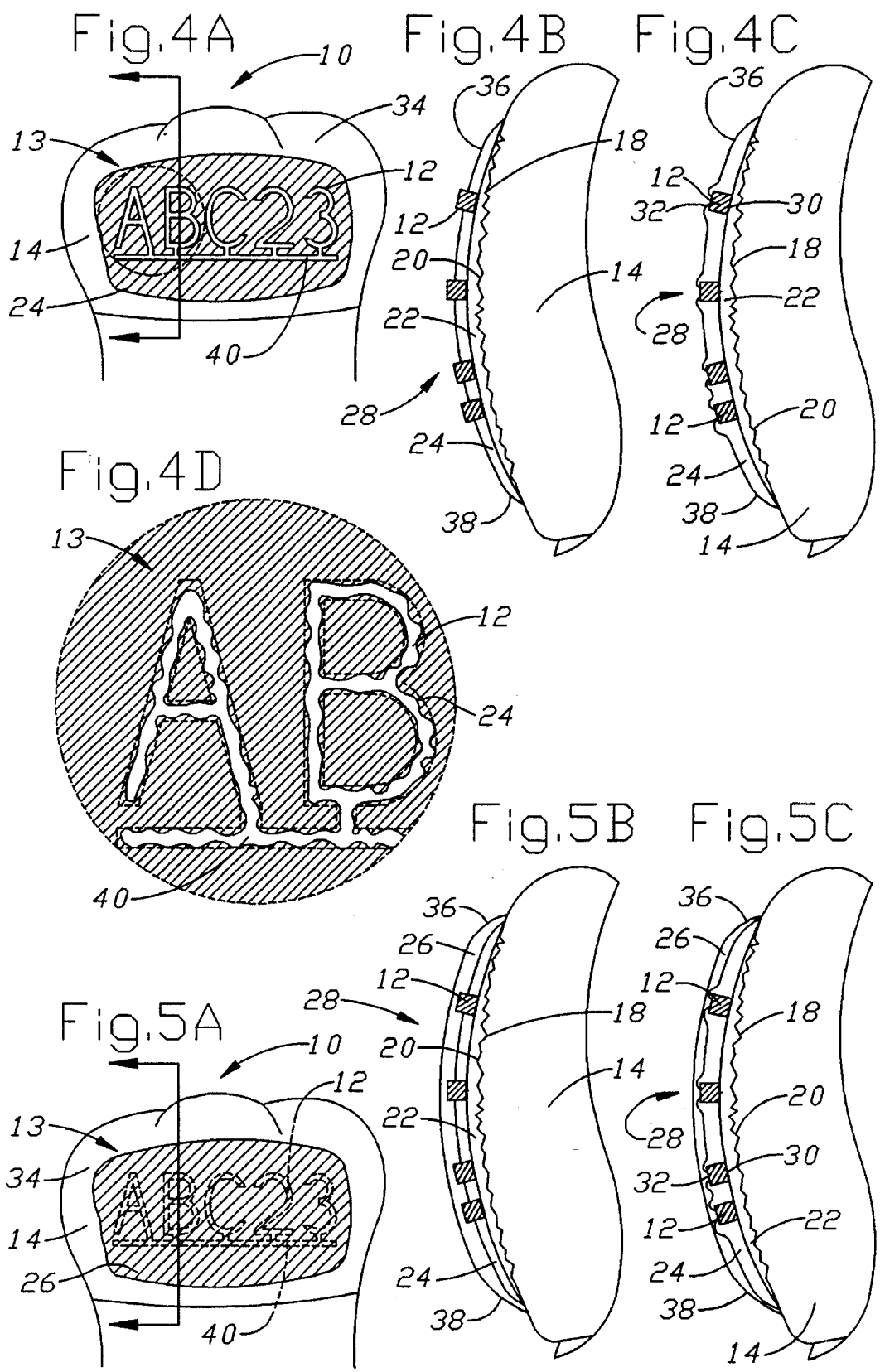

RADIOGRAPHICALLY READABLE INFORMATION CARRIER AND METHOD OF USING THE SAME

BACKGROUND OF THE INVENTION

1. Field of the Invention

The present invention relates to a permanent, personal information carrier for placement on a tooth, and, more particularly, to such a carrier in which the information of said carrier is directly readable by means of a standard dental X-ray radiographs or the like and method of using same.

2. Description of the Related Art Including Information Disclosed Under 37 CFR 1.97–1.99

There are numerous techniques known for permanently marking a person by permanently affixing an information carrier to the person identified. There are two known basic techniques of affixing the carrier to the person, and they both usually employ means for attaching the carrier to a tooth because of its relative durability and accessibility. In the first technique, the carrier is inserted into either a naturally occurring cavity resulting from drilling out unwanted decay or a manufactured cavity resulting from drilling out a healthy tooth, which is then filled with a filler to protectively seal the information carrier within the cavity. This provides maximum protection for the carrier.

Disadvantageously, with this first technique, it has not been known how to conceal the presence of the carrier while at the same time enabling reading of the carrier without the wearer undergoing intrusive invasive surgery of drilling the tooth to have the required cavity to hold the information carrier. In U.S. Pat. No. 5,044,955 issued to Jagmin on Sep. 3, 1991, a radiographically detectable carrier is installed in a cavity in the side of a person's tooth which is filled with a radiolucent composite filler to protectively seal the carrier within the cavity. The filler is visually opaque and matches the color of the surrounding tooth surface which conceals the presence of the personal information carrier. This carrier is readable by X-ray machines without the need to excavate the tooth. This enables reading the information without first excavating the carrier while still concealing the presence of the carrier, but, disadvantageously, the tooth must be drilled to have the required cavity to hold the information carrier and this results in intrusive invasive surgery for the wearer.

A principal problem with requiring intrusive invasive surgery to insert the carrier to the tooth arises primarily in the case of people who are unwilling to undergo intrusive surgery to have the carrier inserted into their tooth. In those instances, if the person is unwilling to undergo surgery, in all likelihood, the person will refuse to have the carrier inserted and there will be no possibility of identification of the person at a later date.

In the second known technique, information carrying marks or other indicia are attached onto the surface of the tooth. This enables reading the information without first excavating the carrier and securing the carrier without any intrusive invasive surgery. Disadvantageously, the carrier is not radiographically readable, therefore, special experience and special code reading devices are required to read the carrier and these devices are not conveniently located in medical or dental clinics to read the information. In U.S. Pat. No. 4,557,693 issued to Elggren on Dec. 10, 1985, a carrier attached to the lingual surface, or tongue side, surface of a tooth, with a clear polymer placed over the carrier, can be read through use of a special electronic photo-optical reader and not through conventional X-ray devices. Similarly, in International Patent No. WO 86/00213 issued to Maxwell et al. on Jan. 16, 1986, a disc made of photographic film carries the identifying indicia and the disc is radiotransparent or radiotranslucent under X-rays so it cannot be read by conventional X-ray devices. Also, in U.S. Pat. No. 3,925,896 issued to McDowell on Dec. 16, 1975, coded tines are inlaid into a surface of a tooth at selected radial positions to encode identifying information and once the pattern is placed in the dental work, the code may be read by photographing and enlarging the pattern and placing an overlay over the enlarged portion. The code can not be concealed and still be readable without invasive surgery on the tooth.

In this second known technique, information carrying marks or other indicia are attached onto the surface of the tooth which enables reading the information without first excavating the carrier and securing the carrier without any intrusive invasive surgery, but disadvantageously, the presence of the carrier cannot be concealed because it is not radiographically readable. A principal problem with not concealing the presence of the carrier from casual visual inspection arises primarily in the case of kidnapping. In those instances, if the kidnapper discovers the presence of an identification marking on a child, in all likelihood, the carrier will be removed, perhaps by removing the entire tooth. If the carrier is not detected and removed, then it may be detected in the course of routine dental X-rays which can then be reported to the appropriate authorities.

SUMMARY OF THE INVENTION

It is therefore the principal object of the present invention to provide an identification apparatus having a personal information carrier having information carried by a radiopaque configuration which is radiographically discernable with the personal information carrier secured to an external and noninvasive portion of a tooth.

It is a further object of this invention to provide a method for radiographically marking a person with individual information, having the steps of providing a personal information carrier having information carried by a radiopaque configuration which is radiographically readable by conventional dental X-ray technique and securing the personal information carrier to an external and noninvasive portion of a tooth.

Another object of the invention is to provide a method for detection of the location of a missing person having the steps of recording a code uniquely identifying the missing person apart from the others of a group of persons before the person is missing, producing a personal information carrier which has the code outlined in radiopaque material; securing the personal information carrier to an external and noninvasive portion of a tooth; and informing at least one of the (a) police authorities, (b) hospitals, (c) morgues, (d) coroners and (e) the professional dental community of the code of the person after that are missing and how to report the discovered code to the appropriate parties.

Another object of the invention is to provide a method for identifying a missing person having the steps of securing a personal information carrier to an external and noninvasive portion of a tooth having a radiopaque code readable from a radiograph thereof; visually concealing the personal information carrier with a visually opaque and radiolucent material; making a radiograph of the external and noninvasive portion of a tooth to read the code when the person is found and before the person is identified; and comparing the radiographically readable code with the code of the missing person to identify the person.

BRIEF DESCRIPTION OF THE DRAWINGS

The foregoing objects and advantageous features of the invention will be explained in greater detail and others will be made apparent from the detailed description of the preferred embodiments of the present invention which are given with reference to the several figures of the drawing, in which:

FIG. 1A is a buccal view of a tooth in which a portion of the tooth is etched;

FIG. 1B is an enlarged cross sectional view along line 1B—1B of FIG. 1A;

FIG. 2A is a buccal view of a tooth in which a layer of resin overlies a portion of the tooth;

FIG. 2B is an enlarged cross sectional view along line 2B—2B of FIG. 2A;

FIG. 3A is a buccal view of a tooth in which a layer of dental composite overlies a portion of the tooth;

FIG. 3B is an enlarged cross sectional view along line 3B—3B of FIG. 3A;

FIG. 4A is a buccal view of a tooth in which a personal information carrier is disposed in a layer of dental composite overlying a portion of the tooth;

FIG. 4B is an enlarged cross sectional view along line 4B—4B of FIG. 4A showing an embodiment of the invention;

FIG. 4C is an enlarged cross sectional view along line 4B—4B of FIG. 4A showing another embodiment of the invention;

FIG. 4D is an enlarged plan view of that which is circled and designated as 4D in FIG. 4A;

FIG. 5A is a buccal view of a tooth in which another layer of dental composite overlies the personal information carrier;

FIG. 5B is an enlarged cross sectional view along line 5B—5B of FIG. 5A showing an embodiment of the invention; and FIG. 5C is an enlarged cross sectional view along line 5B—5B of FIG. 5A showing another embodiment of the invention.

DESCRIPTION OF THE PREFERRED EMBODIMENTS

Referring now to the drawings, the apparatus and methodology of the subject invention involve the proper preparation, securement and use of personal information carrier 12 on external and noninvasive portion of a tooth 14 of an individual for the purpose of providing immediate accessibility to information, personal identification and other pertinent data. Such information might be immediately required, for example, to provide identification in a kidnapping situation. Personal information carrier 12 literally becomes part of an individual's anatomy and is not subject to being misplaced, forgotten or separately damaged. Nevertheless, no invasive techniques are required for its securement. Additionally, personal information carrier 12 requires no conscious effort or attention to maintain. Further, personal information carrier 12 is radiographically discernable which allows for personal information carrier 12 to be concealable yet still discernable without invasive techniques being used for its securement or discernability.

An example of an identification apparatus 10 is shown in FIGS. 4A and 4D and comprises personal information carrier 12 having information carried by radiopaque configuration 12 which is radiographically discernable and means for securing 13 personal information carrier 12 to external and noninvasive portion of a tooth 14.

The term "noninvasive" means that no entry into the tooth structure or other part of the body is necessary to secure personal information carrier 12. In other words, there is no requirement to drill out unwanted decay in a natural occurring cavity or to manufacture a cavity resulting from drilling out a healthy tooth to secure personal information carrier 12 to external and noninvasive portion of a tooth 14. The fact that personal information carrier 12 can be secured directly to the surface of a tooth is a significant feature of the present invention. Prior art usage of the tooth structure in connection with identification tags has involved invasive and often painful techniques of drilling into the enamel, the present invention offers no such disadvantage. Rather, than frightening children and adults, the securement procedure required for personal information carrier 12 are simple, quick and without significant discomfort. Since all phases of securement and detection of personal information carrier 12 involve noninvasive techniques which are applied only with respect to the surface of the tooth, there need be no use of needles, drills or other equipment which tends to alarm the patient.

An example of personal information carrier 12 as shown in FIG. 5A, comprises a radiopaque material that is compatible in use within a human body environment, such as metals that are inert to many chemical reactions such as gold, silver, metal alloys resistant to high temperatures, or metal alloys used for dental crowns or dental bridges, or any suitable radiopaque material known in the field, from which the shapes of code characters have been formed. The term "radiopaque" means that the information carried by radiopaque configuration 12 is radiographically discernable through noninvasive visualizing techniques such as conventional X-ray equipment found in dental offices and doctor offices. Personal information carrier 12 preferably has a relatively high melting point to prevent loss of identification information in the event of fire.

Preferably, radiopaque configuration 12 includes alphanumeric code characters 12 which are formed at various locations to provide an identification code word for uniquely identifying one of a large group of individuals. The capital letters I and O and the lower case 1 are not used to avoid confusing them with numerical one or zero. With a five character code using capital letters and numbers, a code word universe of approximately 40,000,000 codes are provided, and if both lower case and upper case letters are used in combination with numbers, approximately 500,000,000 codes are provided, which is believed are more than sufficient for all current practical purposes.

As shown in FIGS. 4D and 5A, the letters consist of radiopaque material which has been externally shaped to form positive, or darkened images of the alphanumeric characters 12. Preferably, the body of each character is relatively wide for optimum readability and is entirely filled with radiopaque materials. Alphanumeric characters 12 are held together in proper sequence by means of thin interconnecting strip 40 of the same radiopaque material from which the code characters 12 are made. A preferable overall size for personal information carrier 12 is 5.0 millimeters long and 2.0 millimeters high and 0.1 millimeters thick.

Referring to FIGS. 4A, 4D, 5A and 5B, the size of personal information carrier 12 is of a dimension smaller than patch member 28. In other words, personal information carrier 12 has to be sufficiently small to be secured to exterior portion of a tooth 14. In cases of a small child, a four code character code may be used in order to fit it on a smaller personal information carrier 12 without reducing the size and readability of characters 12.

Personal information carrier 12, itself, can be very thin and still be radiopaque. The thickness of approximately 0.1 mils has been found to be sufficient to maintain structural integrity of personal information carrier 12 from the preferred radioactive material noted above.

Most significantly about the size of personal information carrier 12 is that the alphanumeric code characters 12 are sufficiently large to be readable with the unaided eye, having a height of approximately 1.6 millimeters with a character field width of approximately 1.0 millimeters. Thus, when a routine dental X-ray is taken, a four or five alphanumeric code word can be immediately read. The code word is then decoded by comparing the code word to a plurality of code words in a directory of missing persons. In keeping with one aspect of the invention, such a directory is distributed to the police authorities, hospitals, morgues, coroners and the professional dental community along with directions and telephone numbers of the appropriate parties to contact in the event of discovery of the code of a missing person.

Alphanumeric codes are preferred because of ease in readability and ease of indexing by alphabetic and numeric order in the directory of missing persons. Other coding, such as bar code characters, binary characters, or other shapes, can also be used according to the method, so long as the shapes of the lines, dots or other characters which comprise the codes are discernable via X-ray radiograph.

Generally, personal information carrier 12 can be sized to be secured to any external and noninvasive portion of a tooth 14. However, preferably a tooth of maximum mesial distal proportion or width, which has the least amount of restoration is selected for the securement of personal information carrier 12. In the case of a small child, if the permanent first molar has not erupted, the primary, or deciduous, second molar is selected. However, if the permanent upper first molar has erupted, it should be used since it will usually be the largest tooth in the mouth.

Also, referring to FIG. 5A, while personal information carrier 12 can be secured on either outer buccal, or cheek side, or inner lingual 34, or tongue side of the tooth, there is less chance of distortion on an intraoral X-ray using a periapical or bitewing X-ray film on the lingual or inner side.

Typically, the securement of personal information carrier 12 will occur in a dental office, and might easily be accomplished in connection with a normal patient visit. Referring to FIGS. 1A and 1B, the enamel surface of external and noninvasive portion of a tooth 14 is first isolated, pumiced and rinsed to produce a clean enamel surface. Securing means 13 includes etched portion 18 of external and noninvasive portion of a tooth 14 overlying external and noninvasive portion of a tooth 14. Etched portion 18 is accomplished by conventional acid etch techniques involving swabbing a solution of 10% phosphoric acid or other suitable acid that removes organic layer of enamel over external and noninvasive portion of a tooth 14. Etched portion 18 is then rinsed and dried.

Referring to FIGS. 2A and 2B, securing means 13 includes resin layer 22 overlying external and noninvasive portion of a tooth 14. The purpose of having etched portion 18 is to provide a rough surface 20 which will enable a strong mechanical bond with resin layer 22. Resin layer 22 is then light cured for approximately 20 seconds.

Referring now to FIGS. 3A and 3B, securing means 13 includes layer of dental composite 24 overlying external and noninvasive portion of a tooth 14. In preferred materials the commonly used dental composite is typically chemically interactive or bonded to one another. Without such compatibility, greater care must be exercised in developing a stronger mechanical bond between layer of dental composite 24 and personal information carrier 12. Thus, a mechanical bond between dental composite layer 24 and personal information carrier 12 should be secured to insure a greater securement means, particularly within the mouth environment where large shear forces can be exerted.

In referring to FIGS. 4A and 4B, with layer of dental composite 24 in place and prior to the hardening of layer of dental composite 24, personal information carrier 12 is then disposed into layer of dental composite 24 overlying external and noninvasive portion of a tooth 14 with characters 12 facing preferably outwardly from surface of external and noninvasive portion of the tooth 14. Personal information carrier 12 is secured to lingual side 34 of external and noninvasive portion of the tooth 14 or to the buccal side of external and noninvasive portion of the tooth 14. Layer of dental composite 24 is light cured for approximately 20 seconds. This embodiment works, but there is no extra mechanical bond secured between dental composite layer 24 and personal information carrier 12 to help maintain the securement of personal information carrier 12 to layer of dental composite 24.

Referring to FIGS. 4A, 4C and 4D, in another more preferred embodiment, personal information carrier 12 is at least partially submerged into layer of dental composite 24. Personal information carrier 12 has side 30 and opposing side 32 in which layer of dental composite 24 overlies at least a portion of side 30 and at least a portion of opposing side 32. This preferred embodiment provides the mechanical bond between dental composite layer 24 and personal information carrier 12 to help maintain the securement between dental composite layer 24 and personal information carrier 12 while still maintaining the radiographic discernability of personal information carrier 12. Additionally, the mechanical bond between dental composite layer 24 and personal information carrier 12 resists shear forces resulting from chewing, eating hard foods, brushing teeth, etc.

Any radiolucent composite will suffice for the composition of layer of dental composite 24. A preferred radiolucent layer of dental composite 24 which can be used is Herculite XR®, a registered trademark product made by Kerr, Inc. Radiolucency of layer of dental composite 24 is of the utmost importance, so that the shapes of the radiopaque configuration 12 can be recorded radiographically and read. If the selected tooth has previously been restored with radiopaque composite, then this radiopaque composite must be removed and replaced with radiolucent composite 24 to prevent difficulty in reading personal information carrier 12.

Referring to FIGS. 4A and 5B, personal information carrier 12 includes means of concealing personal information carrier 12 overlying external and noninvasive portion of a tooth 14. The concealing means is layer of dental composite 24 which is visually opaque as well as radiolucent. Additionally, layer of dental composite 24 has a coloration substantially similar to the coloration of tooth 14 so when at least a portion of layer of dental composite 24 overlies personal information carrier 12, personal information carrier 12 is concealed from visual inspection yet personal information carrier 12 is able to still be radiographically discernable through conventional X-rays due to layer of dental composite 24 being radiolucent. Layer of dental composite 24 is light cured for approximately 40 seconds.

Referring to FIGS. 5A, 5B and 5C, the concealing means also can include another dental composite layer 26 overlying external and noninvasive portion of a tooth 14. Another layer of dental composite 26 is visually opaque and radiolucent and has a coloration substantially similar to the coloration of tooth 14 so when at least a portion of layer of dental composite 24 overlies personal information carrier 12, personal information carrier 12 is concealed from visual inspection yet personal information carrier 12 is able to still be radiographically discernable through conventional X-rays due to another layer of dental composite 26 being radiolucent. Another layer of dental composite 26 is lightly cured for 20 seconds.

Personal information carrier 12 is concealed to reduce the risk of removal, or more likely, removal of the entire tooth 14 from a missing child by a kidnapper or the like to elude detection and capture. If a kidnapper knows of the presence of personal information carrier 12, he or she will have it removed. If not, the first time the child or other person who is brought in for routine dental X-rays, which are often requires for admission to school, or which otherwise occur routinely or sometimes to diagnose a dental problem which arises, the missing person will be positively located.

In the case of an adult or child who has been made aware of the presence of personal information carrier 12 in their tooth 14, a strategy to enhance discovery would be for them to feign a tooth ache to induce their kidnapper into taking them to a dentist for X-rays.

In the case of persons who have died and whose bodies have been recovered but not identified, routine X-rays will immediately reveal the presence of personal information carrier 12. Moreover, the X-ray exposure or duplicates can be easily kept in various public and private files as a record of the positive identification provided by this invention. Advantageously, after reading code 12, personal information carrier 12 remains within the body for later confirmation of identification, if required.

Referring to FIGS. 5A, 5B and 5C, concealing means 13, as described above includes layer of dental composite 24 and/or another dental composite layer 26 overlying personal information carrier 12 often takes the configuration of a patch member 28 which also overlies external and noninvasive portion of a tooth 14. Patch member 28 has edges 36, 38 which are feathered. Edges 36, 38 are also smoothed. Feathering and smoothing edges 36, 38 operate to prevent any areas from the inside of the mouth being cut by rough edges and provide further visual concealment of personal information carrier 12. Edges 36, 38 are then polished with finished burs, discs or polishing paste.

After the securement of personal information carrier 12 to external and noninvasive portion of a tooth 14, an intraoral, periapical X-ray exposure is taken to confirm the readability of the code word of personal information carrier 12.

With personal information carrier 12 properly secured to external and noninvasive portion of a tooth 14, the information should be secure for many years, yet readily available for immediate access in case of emergency or other conditions requiring use.

Personal information carrier 12 is sold in combination with a package and a set of instructions for securing personal information carrier 12 to external and noninvasive portion of the tooth 14.

This invention provides a method of radiographically marking a person with individual information which comprises the steps of providing personal information carrier 12 having information carried by radiopaque configuration 12 which is radiographically readable by conventional dental X-ray techniques; and securing personal information carrier 12 to external and noninvasive portion of a tooth 14. The steps of etching 18, applying resin layer 22, applying layer of dental composite 24, securing personal information carrier 12, applying layer of another dental composite 26 overlying external and noninvasive portion of a tooth 14, and feathering, smoothing and polishing edges 36, 38 of patch member 28 as set forth in great detail above, apply to this method of radiographically marking a person with individual information. The step of securing also includes concealing the personal information carrier 12 with a visually opaque radiolucent material that is substantially similar to the coloration of the tooth 14, as more fully set forth above.

Additionally, as more fully set forth above, the securement of personal information carrier 12 to external and noninvasive portion of a tooth 14 of the method of radiographically marking a person with individual information includes disposing personal information carrier 12 into layer of dental composite 24 or where personal information carrier 12 is at least partially submerged into layer a of dental composite 24.

Another method of detection of the location of a missing person is provided by this invention which includes the steps of recording a code 12 which often can take the form of numbers, letters and other identifiable forms which uniquely identifying the missing person apart from the others of a group of persons before the person is missing, producing personal information carrier 12 which has code 12 outlined in radiopaque material; securing personal information carrier 12 to external and noninvasive portion of a tooth 14; and informing at least one of the (a) police authorities, (b) hospitals, (c) morgues, (d) coroners and (e) the professional dental community of the code 12 of the person after that are missing and how to report the discovered code to the appropriate parties.

Another method of this invention is to provide a method for identifying a missing person having the steps of securing personal information carrier 12 to external and noninvasive portion of a tooth 14 having radiopaque code 12 readable from a radiograph thereof; visually concealing personal information carrier 12 with a visually opaque and radiolucent material; making a radiograph of external and noninvasive portion of a tooth 14 to read the code when the person is found and before the person is identified; and the comparing radiographically readable code with the code 12 of the missing person to identify the person.

While a detailed description of the preferred embodiment of the invention has been given, it should be appreciated that many variations can be made thereto without departing from the scope of the invention set forth in the appended claims.

We claim:

1. An identification apparatus comprising:
   a personal information carrier having information carried by a radiopaque configuration which is radiographically discernable;
   means for securing the personal information carrier to an external and noninvasive portion of a tooth; and
   means for visually concealing the personal information carrier in which the concealing means includes a patch member for overlying the personal information carrier and the external and noninvasive portion of a tooth.

2. The personal information carrier of claim 1 in which the securing means includes a resin layer for overlying the external and noninvasive portion of a tooth.

3. The personal information carrier of claim 1 in which the securing means includes a layer of dental composite for overlying the external and noninvasive portion of a tooth.

4. The personal information carrier of claim 3 in which the layer of dental composite substantially matches the color of the tooth to conceal the presence of the layer of dental composite.

5. The personal information carrier of claim 3 in which the personal information carrier is disposed into the layer of dental composite.

6. The personal information carrier of claim 5 in which the personal information carrier is at least partially submerged into the layer of dental composite.

7. The personal information carrier of claim 6 in which the personal information carrier has a side and an opposing side in which the layer of dental composite overlies at least a portion of the side and at least a portion of the opposing side.

8. The personal information carrier of claim 1, in which the concealing means is visually opaque.

9. The personal information carrier of claim 1, in which the concealing means is radiolucent.

10. The personal information carrier of claim 1 in which the concealing means includes at least a portion of the layer of dental composite for overlying the external and noninvasive portion of a tooth.

11. The personal information carrier of claim 1 in which the concealing means includes another layer of dental composite for overlying the personal information carrier.

12. The personal information carrier of claim 11 in which the layer of another dental composite substantially matches the color of the tooth to conceal the presence of the layer of another dental composite.

13. The personal information carrier of claim 1 in which the patch member has edges which are feathered.

14. The personal information carrier of claim 1 in which the patch member has edges which are smoothed.

15. The personal information carrier of claim 1 in which the patch member has edges which are polished.

16. The personal information carrier of claim 1 in which the personal information carrier is of a dimension smaller than the patch member.

17. The personal information carrier of claim 1, in combination with a dental X-ray machine for providing a radiographic reproduction of the radiopaque configuration on radiographic film.

18. The personal information carrier of claim 1, in combination with a decoder for decoding a code represented by the radiopaque configuration.

19. The personal information carrier of claim 1, in which the radiopaque configuration include configurations of alphanumeric code words.

20. The personal information carrier of claim 1, in combination with a package within which the personal information carrier and a set of instructions for securing the personal information carrier to the external and noninvasive portion of the tooth are enclosed.

21. The personal information carrier of claim 1, which includes means for utilizing a radiopaque, sensing, noninvasive, visualizing technique to convey information.

22. The personal information carrier of claim 21, in which the noninvasive technique is standard radiographic X-ray technique for forming a radiographic representation of the radiopaque configuration of alphanumeric characters.

23. The personal information carrier of claim 1, in which the personal information carrier is adapted to be secured to a buccal side of the external and noninvasive portion of the tooth.

24. The personal information carrier of claim 1, in which the personal information carrier is adapted to be secured to a lingual side of the external and noninvasive portion of the tooth.

25. The personal information carrier of claim 1, in which the securing means includes a resin layer for overlying the external and noninvasive portion of a tooth, a layer of dental composite overlying the resin layer and in which the personal information carrier is disposed into the layer of dental composite.

26. The personal information carrier of claim 25, in which the concealing means includes another layer or dental composite for overlying the layer of dental composite and the personal information carrier.

27. A method of radiographically marking a person with individual information, comprising the steps of:

providing a personal information carrier having information carried by a radiopaque configuration which is radiographically readable by conventional dental X-ray technique;

securing the personal information carrier to an external and noninvasive portion of a tooth; and concealing visually the personal information carrier.

28. The radiographically marking method of claim 27 in which the step of securing includes the step of etching the external and noninvasive portion of a tooth.

29. The radiographically marking method of claim 27 in which the step of securing includes the step of applying a resin layer to overlie the external and noninvasive portion of a tooth.

30. The radiographically marking method of claim 27 in which the step of securing includes the step of applying a layer of dental composite to overlie the external and noninvasive portion of a tooth.

31. The radiographically marking method of claim 30 in which the personal information carrier is disposed into the layer of dental composite.

32. The radiographically marking method of claim 30 in which the personal information carrier is at least partially submerged into the layer of dental composite.

33. The radiographically marking method of claim 30 in which the personal information carrier has a side and an opposing side in which the layer of dental composite overlies at least a portion of the side and at least a portion of the opposing side.

34. The radiographically marking method of claim 30 in which the layer of dental composite has a coloration substantially similar to the coloration of a tooth.

35. The radiographically marking method of claim 27 in which the step of concealing includes applying a visually opaque material to overlie the personal information carrier.

36. The radiographically marking method of claim 27 in which the step of concealing includes applying a radiolucent material to overlie the personal information carrier.

37. The radiographically marking method of claim 27 in which the step of concealing the personal information carrier includes the step of applying a layer of another dental composite to overlie the personal information carrier.

38. The radiographically marking method of claim 35 in which the another layer of dental composite is visually opaque, radiolucent and has a coloration substantially similar to the coloration of the tooth.

39. The radiographically marking method of claim 27 in which the step of securing includes a patch member overlying the external and noninvasive portion of a tooth.

40. The radiographically marking method of claim 39 including the step of feathering an edge of the patch member overlying the external and noninvasive portion of a tooth.

41. The radiographically marking method of claim 39 including the step of smoothing a least a portion of the patch member overlying the external and noninvasive portion of a tooth.

42. The radiographically marking method of claim 39 including the step of polishing a portion of the patch member overlying the external and noninvasive portion of a tooth.

43. The radiographically marking method of claim 27 including the step of taking an X-ray radiograph of the radiopaque configurations to read the information.

44. The radiographically marking method of claim 27 in which the radiopaque configuration includes characters including the step of decoding the characters to ascertain the information carried by said characters.

45. The radiographically marking method of claim 27 including the step of encoding information by providing the radiopaque configuration in the form of characters to identify the person.

46. The radiographically marking method of claim 45 in which said encoding means includes alphanumeric characters which uniquely identify the person.

47. The radiographically marking method of claim 27 including the step of replacing any radiopaque reconstruction of the tooth that would interfere with readability of the radiopaque personal information carrier with radiolucent composite material.

48. The radiographically marking method of claim 27 including the step of locating the external and noninvasive portion of the tooth with no decay and minimum prior reconstruction.

49. The radiographically marking method of claim 27 in which the step of securing includes securing said carrier to a buccal side of the external and noninvasive portion of the tooth.

50. The radiographically marking method of claim 27 in which the step of securing includes securing said carrier to a lingual side of the external and noninvasive portion of the tooth.

51. A method of detection of the location of a missing person comprising the steps of:

recording a code uniquely identifying the missing person apart from the others of a group of persons before the person is missing;

producing a personal information carrier which has the code outlined in radiopaque material;

securing the personal information carrier to an external and noninvasive portion of a tooth; and concealing visually the personal information carrier; and informing at least one of the (a) police authorities, (b) hospitals, (c) morgues, (d) coroners and (e) the professional dental community of the code of the person after they are missing and how to report the discovered code to the appropriate parties.

52. The detection method of claim 51 in which the step of concealing includes applying a layer of visually opaque material to overlie the personal information carrier.

53. The detection method of claim 51 in which the step of concealing includes applying a layer of radiolucent material to overlie the personal information carrier.

54. The detection method of claim 51 including the step of taking an X-ray radiograph of the radiopaque configurations to read the information carrying characters thereof.

55. A method for identifying a missing person comprising the steps of:

securing a personal information carrier to an external and noninvasive portion of a tooth, having a radiopaque code readable from a radiograph thereof;

concealing visually the personal information carrier including overlying the personal information carrier with a thickness of a visually opaque and radiolucent material in which the material is substantially similar in color to the coloration of the tooth and in which at least a portion of the material which extends beyond overlying the personal information carrier tapers down in thickness;

making a radiograph of the external and noninvasive portion of a tooth to read the code when the person is found and before the person is identified; and comparing the radiographically readable code with the code of the missing person to identify the person.

* * * * *